US008173797B2

(12) United States Patent
Meinwald et al.

(10) Patent No.: US 8,173,797 B2
(45) Date of Patent: May 8, 2012

(54) THERAPEUTIC COMPOUNDS DERIVED FROM SPIDER VENOM AND THEIR METHOD OF USE

(75) Inventors: Jerrold Meinwald, Ithaca, NY (US); Andrew Edmund Taggi, Ithaca, NY (US); Frank Clemens Schroeder, Ithaca, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 989 days.

(21) Appl. No.: 11/572,357

(22) PCT Filed: Jul. 21, 2005

(86) PCT No.: PCT/US2005/026047
§ 371 (c)(1),
(2), (4) Date: Nov. 5, 2007

(87) PCT Pub. No.: WO2006/130161
PCT Pub. Date: Dec. 7, 2006

(65) Prior Publication Data
US 2008/0193452 A1 Aug. 14, 2008

Related U.S. Application Data

(60) Provisional application No. 60/589,746, filed on Jul. 21, 2004.

(51) Int. Cl.
*C07H 17/02* (2006.01)
*C07H 19/00* (2006.01)
*C07H 19/048* (2006.01)

(52) U.S. Cl. .......... 536/27.81; 536/17.5; 536/17.6; 536/27.2; 536/27.21; 536/27.8

(58) Field of Classification Search .......... None
See application file for complete search history.

(56) References Cited

U.S. PATENT DOCUMENTS

| | | | |
|---|---|---|---|
| 5,196,204 A | 3/1993 | Jackson et al. | |
| 5,281,693 A | 1/1994 | Jackson et al. | |
| 5,438,130 A * | 8/1995 | Goldin et al. | 536/27.81 |
| 5,641,492 A | 6/1997 | Sprouse et al. | |
| 5,714,468 A | 2/1998 | Binder | |
| 5,872,107 A | 2/1999 | Schinazi et al. | |
| 5,891,684 A | 4/1999 | Usman et al. | |
| 5,904,922 A | 5/1999 | Carroll | |
| 6,139,845 A | 10/2000 | Donovan | |
| 6,358,513 B1 | 3/2002 | Voet et al. | |
| 6,365,164 B1 | 4/2002 | Schmidt | |
| 6,368,605 B1 | 4/2002 | Donovan | |
| 6,384,026 B1 | 5/2002 | Schroeder et al. | |
| 6,416,765 B1 | 7/2002 | Donovan | |
| 6,565,870 B1 | 5/2003 | Donovan | |
| 6,585,993 B2 | 7/2003 | Donovan et al. | |
| 6,620,415 B2 | 9/2003 | Donovan | |
| 6,638,739 B2 | 10/2003 | Classen | |
| 2004/0127436 A1 | 7/2004 | Daifuku et al. | |

OTHER PUBLICATIONS

Egami et al., Bulletin of the Chemical Society of Japan, 1955, vol. 28, 666-668.*
Arnold et al., "Cytidine 5'-sulfate and Related Nucleotide Analogs", Journal of Organic Chemical Society, 1962, vol. 84, 1406-1411.*
Wigler et al., Journal of the American Chemical Society, 1964, 86(8), 1636-1639.*
Agarwal et al., Experientia, 1965, 21(8), 432-33.*
Chantot et al., Biochimie, 1974, 56(4) pp. 501-507.*
Written Opinion of the International Searching Authority, International Application No. PCT/US2005/026047, dated Mar. 24, 2008;
International Search Report, International Application No. PCT/US2005/026047, dated Mar. 24, 2008.
Munns, et al., Antibody-nucleic acid complexes. Identification of antigenic determinant of a murine monoclonal antibody specific for single-strained nucleic acids, Biochemistry, Jun. 8, 1982 21(12), pp. 2929-2936, Abstract.
Davletov, et al., Isolation and Biochemical Characterization of a Ca2+-independent alpha-Latrotoxin-binding Protein. J. Biol. Chem., Sep. 20, 1996; 271(38), pp. 23239-23245.
The Royal Society of Chemistry, Carbohydrate Chemistry, vol. 33, Chapter 20; Nucleosides, 2002, pp. 275.

* cited by examiner

*Primary Examiner* — Traviss C McIntosh, III
(74) *Attorney, Agent, or Firm* — Janine M. Susan, Esq.; Jacob N. Erlich, Esq.; Burns & Levinson, LLP

(57) ABSTRACT

The present invention is directed to new therapeutic compounds isolated from spider venom and methods of using these new compounds. The compounds are sulfated nucleoside derivatives including ribonucleoside mono- and disulfates derived from guanine, adenosine, and cytidine. Some of these compounds are glycosylated or fucosylated bearing one or more sugar residues.

5 Claims, 7 Drawing Sheets

NOESY correlations

Molecular model of natural product 2

THERAPEUTIC COMPOUNDS DERIVED FROM SPIDER VENOM AND THEIR METHOD OF USE

STATEMENT OF GOVERNMENT INTEREST

The government may have certain rights to aspects of the present invention, pursuant to research funding under grants NIH R01-GM53830.

FIELD OF THE INVENTION

The present invention pertains to new therapeutic compounds derived from spider venom and their methods of use.

BACKGROUND OF THE INVENTION

With almost 40,000 described species, spiders are second only to insects as the most diverse group of animals on land. In attaining this diversity, spiders have evolved sophisticated chemical weapons, which makes them an attractive target for chemical prospecting. Recent drug candidates developed from spider venom components block the neuronal nicotinic acetylcholine receptor, increase parathyroid hormone (PTH) secretion and inhibit atrial fibrillation, the most common chronic cardiac arrhythmia.

Spider venoms, like those of other venomous animals, consist of complex mixtures of biologically active compounds. The primary small-molecule toxins are often acylpolyamines (with over one hundred structures having been described), though the venom may also contain nucleosides, polypeptides, proteins (including enzymes) as well as citric acid, monoamines and free amino acids.

Considering the large amount of analytical work on spider venom already published, the recent identification of a member of an entirely new class of spider neurotoxin seemed surprising. Activity-guided screening of the venom of the grass spider, Hololena curta, led to the discovery of the unique venom component HF-7, which is a bis-sulfated glyconucleoside. HF-7 has the uncommon ability to effectively block kainate receptors, in addition to weakly blocking L-type calcium channels.

The discovery of this entirely unexpected natural product suggested that spider venoms might still harbor interesting new classes of neurotoxins. Moreover, considering the multitude of acylpolyamines that can be identified from a single species, it seemed unlikely that HF-7 is the only spider venom component of its kind. The question remains why sulfated nucleosides have not been found in any other previous analysis.

An understanding of the neurotoxins contained within the venom and its mode of action can assist in the development of new therapeutic agents. There is a present need to develop a new class of therapeutic agents based on the neurotoxins elucidated from spider venom.

BRIEF SUMMARY OF THE INVENTION

The present invention is directed to new therapeutic compounds identified as spider venom components as well as synthetic analogs of these compounds (vide infra). The invention is also directed to methods of employing these new spider-derived compounds and their analogs.

One embodiment is directed to the following compounds:

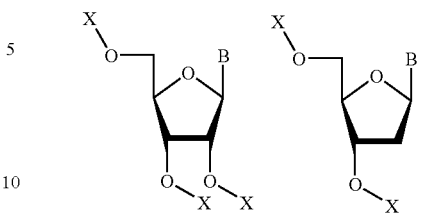

wherein X=H, sulfonate ($SO_3H$), sulfonamide ($SO_2NH_2$), phosphonate ($PO_3H$), fucosyl, glucosyl and various other carbohydrate substituents, including glycosylated and otherwise substituted carbohydrates, whereby at least one X in either of the two structures shown above must be sulfonate ($SO_3H$), wherein B can be:

(1)

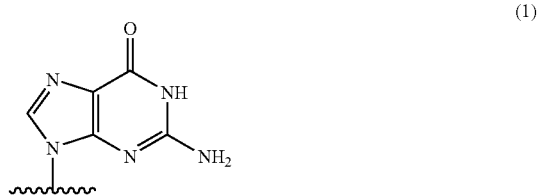

(2)

(3)

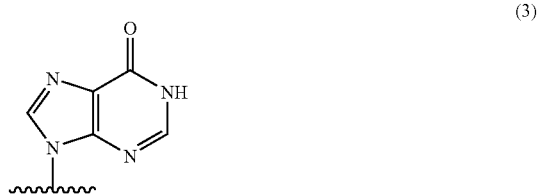

(4)

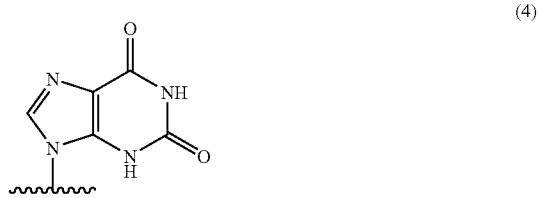

(5)

(6)

-continued (7)

[chemical structure of thymine attached to a wavy bond]

In addition, B can represent other natural and non-natural bases and any other nitrogen-containing heterocycle, including halogenated, for example fluorinated, and/or alkylated, for example methylated derivatives.

In another embodiment, the invention is directed to a method of producing an anti-serum directed to neurotoxins contained within venom. In one aspect, the origin of the venom is from arachnids. Compounds of the present invention, including their respective derivatives, can be used to elicit an immunological response. This process can be used to sensitize a subject's immune system to one or more of the present invention's compounds. Alternatively, an animal can be subjected to one or more of the compounds of the present invention wherein an immunological response is produced. In this scenario, the serum from the animal can be collected and prepared to be used later in the course of treating a person subjected to the introduction of venom.

In another embodiment, one or more compounds (including derivatives thereof) of the present invention are used to treat diseases associated with nuclear events in a cell. These invents include, but are not limited to, transcription and/or translation. In one aspect, the compounds of the present invention can be used to interrupt transcription. In another aspect, the compounds of the present invention can be used to interfere with translation.

For a better understanding of the present invention, together with other and further objects thereof, reference is made to the accompanying drawings and detailed description and its scope will be pointed out in the appended claims.

DETAILED DESCRIPTION OF THE INVENTION

The present invention is directed to new therapeutic compounds identified as spider venom components as well as synthetic analogs of these compounds (vide infra). The invention is also directed to methods of employing these new spider-derived compounds and their analogs.

In one embodiment, the invention is directed toward sulfated nucleoside derivatives. In one aspect, these compounds are ribonucleoside mono- and disulfates derived from guanine, adenosine, and cytidine. In a particular aspect, some of these compounds are glycosylated bearing one or more sugar residues. In one aspect, the sugar residue is D-fucose.

One embodiment is directed to the following compounds:

[two chemical structures of sugar rings with X and B substituents]

wherein X=H, sulfonate (SO3H), sulfonamide (SO2NH2), phosphonate (PO3H), fucosyl, glucosyl and various other carbohydrate substituents, including glycosylated and otherwise substituted carbohydrates, whereby at least one X in either of the two structures shown above must be must be sulfonate (SO3H), wherein B can be one of the compounds selected from Table 1 (below). In addition, B can represent other natural and non-natural bases and any other nitrogen-containing heterocycle, including halogenated, for example fluorinated, and/or alkylated, for example methylated, derivatives.

TABLE 1

Compounds representing B (1)

[chemical structure of guanine]

TABLE 1-continued

Compounds representing B (2) 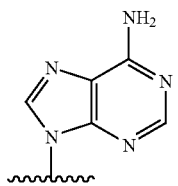

(3) 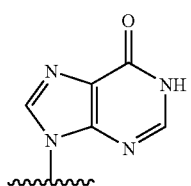

(4) 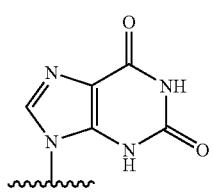

(5) 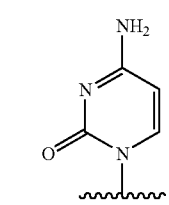

(6) 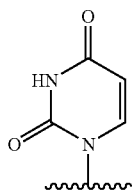

(7) 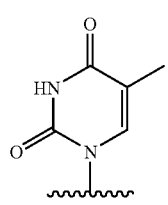

Researchers discovered an entirely unexpected class of neurotoxins (McCormick et al., J. Am. Chem. Soc., 1999, 121, 5661-65, the entire teaching of which is incorporated herein by reference) suggesting that spider venoms still harbor interesting new classes of neurotoxins. Moreover, considering the multitude of acylpolyamines that can be identified from a single spider venom, it seems unlikely that HF-7 is the only spider venom component of its kind. The question remains why sulfated nucleosides have not been found in any other previous analysis. Thus, investigators initiated a program for the characterization of a diverse sampling of spider venoms using a new NMR-based approach. Central to their analytical procedure is the acquisition of a set of NMR spectra of the entire, crude venom without any prior purification, including at a minimum 1H and (1H,1H)-dqf-COSY spectra.

Figure 1:
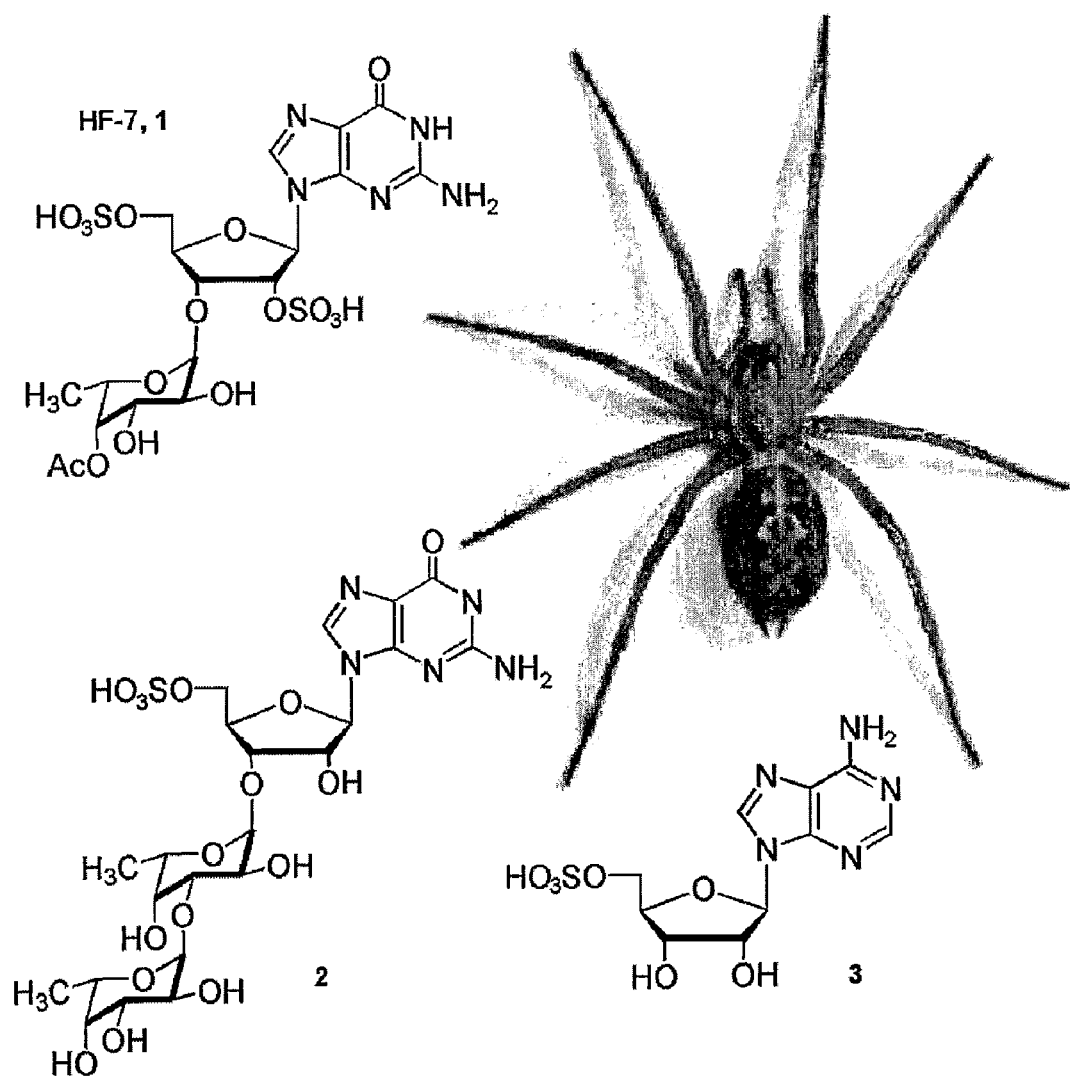
FIG. 1 shows HF-7 (1), isolated from *H. curta*, and a photograph of a female *T. agrestis* with examples of sulfated nucleosides (2, 3) identified from its venom.
Figure 2:
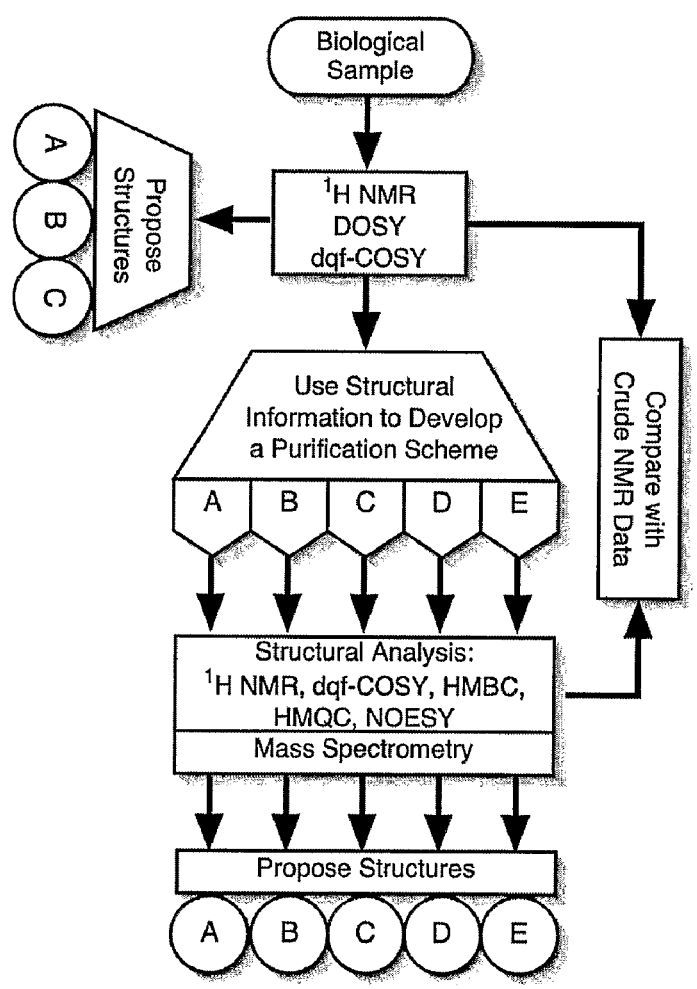
FIG. 2 shows the use of "Direct NMR" for the identification of Natural Products.

In spite of great advances in chromatographic separation technology and analytical instrumentation over the last few decades, the general approach to identification of new natural products has changed very little. This process generally begins with the collection of a large number of specimens, which are then homogenized, lyophilized, and extracted with organic solvents. Subsequent fractionation and characterization of this natural product "soup" is usually motivated by a specific biological activity or sometimes by the suspected presence of novel molecular structures. In this contribution, an improved approach to natural products discovery based on direct NMR-spectroscopic characterization of the biological material prior to any fractionation was pursued (See, FIG. 2).

Apart from the desire to obtain pure compounds for biological testing, isolation of individual compounds is primarily motivated by a perceived need to simplify a mixture prior to structural analysis. Unfortunately, analytical approaches that involve an initial chromatographic step, such as GC or HPLC, are likely to discriminate against some classes of compounds, while favoring others. It appears that in many cases, the structurally unique compounds will often not survive arbitrarily chosen chromatographic conditions, which is why they remain undescribed. (For additional examples of the use of direct NMR analysis to identify unusual natural products from unfractionated mixtures, see Schröder, F. C.; Farmer, J. J.; Attygalle, A. B.; Smedley, S. R.; Eisner, T.; Meinwald, J. Science, 1998, 281, 428-431; Schröder, F. C.; Tolasch, T. Tetrahedron 1998, 54, 12243-12248; Schröder, F.; Sinnwell, V.; Baumann, H.; Kaib, M.; Francke, W. Angew. Chem. Int. Ed. 1997, 36, 77-80; and Schröder, F.; Baumann, H.; Kaib, M.; Sinnwell, V. Chem. Commun. 1996, 2139-2140, the entire teachings of which are incorporated herein by reference). To overcome these difficulties, direct NMR spectroscopic analyses of crude extracts was employed, which provides a much more impartial view of the sample's contents, and in many cases, will already allow for the partial identification of some of the novel compounds present, at the minimum, the acquisition of 1H and (1H,1H)-dqf-COSY spectra. In some cases Diffusion Ordered Spectroscopy (DOSY) also proved useful (Johnson, C. S., Jr. Prog. Nucl. Magn. Reson. Spectrosc. 1999, 34, 203-256; Morris, K. F.; Johnson, C. S., Jr. J. Am. Chem. Soc. 1992, 114, 3139-3141, the entire teachings of which are herein incorporated by reference). In the present invention, the resonances for molecules are arrayed according to size, which can help to deconvolute a mixture. Unfortunately, in areas where the resonances overlap, this experiment leads to streaking instead of discrete peaks. In the case of spider venoms where one has to deal with several closely related structures, this method has proven to be suboptimal.

The utility of NMR spectroscopy to characterize unpurified venom and thus allowing for an impartial view of its contents, without any molecular prejudices resulting from pre-purification (vide infra) is demonstrated by the present invention. Demonstrated herein is the efficacy of this method in characterizing the venom of the Hobo Spider, Tegenaria agrestis, which resulted in the identification of a family of no fewer than 7 new nucleoside-derived natural products.

Screening for new natural products using direct NMR-spectroscopic analyses of crude or partially purified materials has important advantages over solely mass spectroscopy-based approaches. One major disadvantage of using MS as the primary analytical tool is that the appropriate ionization technique can only be determined once initial structural data is available. For example, does the molecule form positively, or negatively charged ions (or neither at all) under electrospray conditions? Does a compound decompose or re-arrange upon ionization? Even if the ionization techniques chosen allow for detection of most of the compounds in a complex natural products mixture, the connectivity information available through 2D NMR spectroscopy represents an invaluable addition to mass-spectroscopic results. Furthermore, any assessment of the quantitative composition of unknown compounds through MS will necessarily be uncertain. Thus, when choosing an exclusively MS-based approach, one may inadvertently exclude entire new structural classes.

From the initially acquired 1D- and 2D-NMR spectra of a mixture, sufficient data can be obtained in order to identify some or all of the components. When this is not the case, the preliminary structural information is used to develop a purification scheme, in such a way as to prevent the unknowns from changing, thus precluding a skewing of the results by the analytical techniques employed. After HPLC separation, the collected fractions are re-analyzed using 1H and dqf-COSY spectra. This information is then compared with the original spectroscopic data to determine if any of the components have undergone degradation or rearrangement. This comparison is essential to determine whether one is identifying natural products rather than degradation products.

One frequent concern when working with biological material suspected to have potent activity is its scarcity. For example, for most spider species the amounts of venom that can be collected are extremely small. Often only a fraction of a microliter of venom can be obtained from one individual. Especially in situations like this it seems prudent to acquire all available NMR-spectroscopic data prior to any mass-spectroscopic analysis, because NMR analysis, as opposed to MS, is non-destructive. A standard set of NMR experiments may include (1H,13C)-Heteronuclear Multiple-Bond Correlation spectroscopy (HMBC), (1H,13C)-Heteronuclear Multiple-Quantum correlation (HMQC) and Nuclear Overhauser Effect Spectroscopy (NOESY). Depending on the situation, specialized experiments such as semi-selective HMBC experiments (Claridge, T. D. W.; Pérez-Victoria, I. Org. Biomol. Chem. 2003, Published on the web Jul. 24, 2003; Gaillet, C.; Lequart, C.; Debeire, P.; Nuzillard, J.; M. J. Magn. Reson. 1999, 139, 454-459, the entire teachings of which are herein incorporated by reference) or a SIMBA (Vogt, F. G.; Benesi, A. J. J. Magn. Reson. 1998, 132, 214-219, the entire teaching of which is herein incorporated by reference) may be needed to provide added information or resolution to a particularly complex spectrum.

After the acquisition of the appropriate NMR spectra, the sample is subjected to the appropriate mass spectrometric techniques. With NMR data in hand, the optimal mass-spectroscopic ionization detection technique is usually quite apparent, and thus structural assignments can be easily completed.

Figure 3:
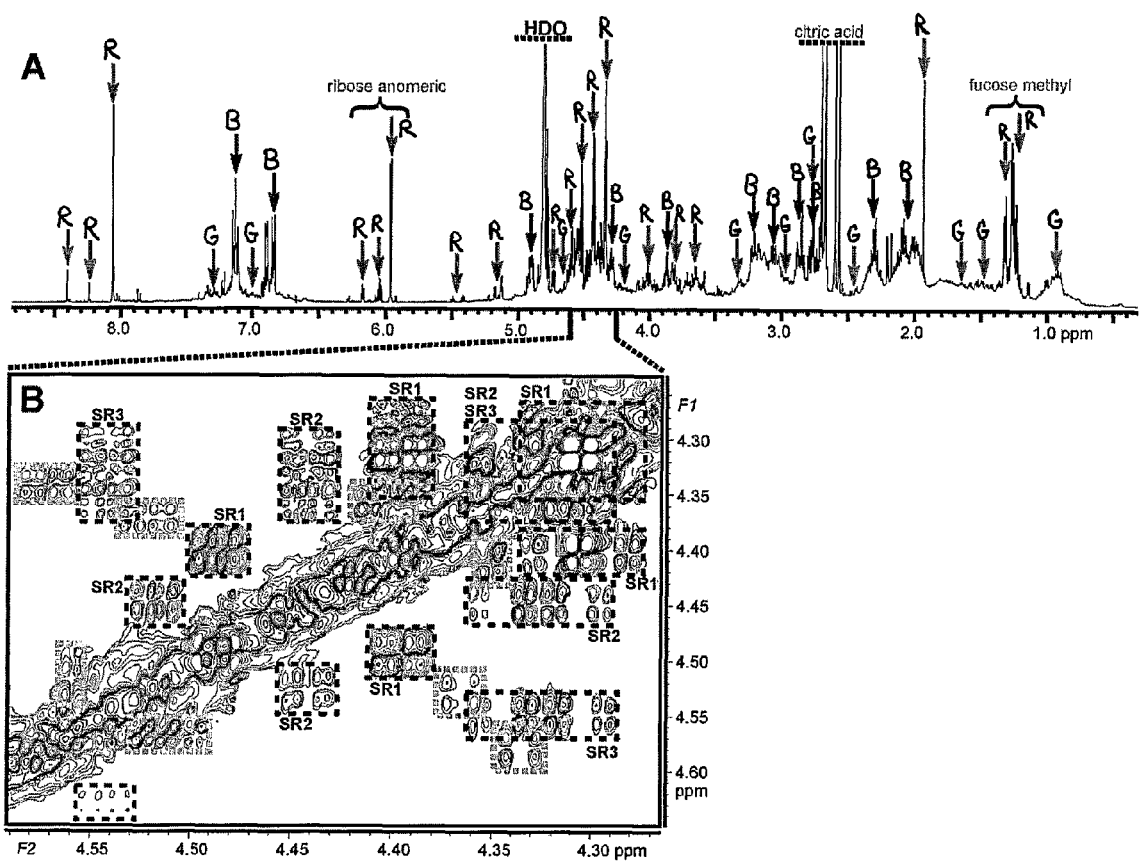
FIG. 3A shows 1H-NMR spectrum of lyophilized, unfractionated Tegenaria agrestis venom in D2O at 500 MHz. Signals marked in red (designated as R) belong to the nucleoside derivatives, signals marked green (designated as G) correspond to proteins, and signals marked blue (designated as B) correspond to polyamines.
FIG. 3B shows a section of the corresponding (1H,1H) dqf-COSY. SR1-SR3: cross peaks of three sulfated ribonucleosides, whereby cross peaks labeled SR1 belong to the major nucleoside in the secretion, guanosine-5'-sulfate (3). Cross peaks marked in green belong to polyamines and peptides. At lower threshold, cross peaks of additional spin systems become visible, among those several corresponding to additional sulfated riboses.

Venom of *T. agrestis* was obtained through electro-stimulation of the venom gland, which causes the spider to release venom into a capillary placed over its fang. This allows for the collection of a pure sample of venom free from digestive proteases that would degrade the venom components. Our analysis of *T. agrestis* began by dissolving the entire lyophilized venom sample (31 mg dry weight corresponding to 235 µL venom) in D2O followed by the acquisition of a 1H NMR spectrum to determine the general composition of the venom sample. At first glance, the resulting spectrum looks extremely messy and complicated, as a consequence of multiply overlapping signals covering almost the entire sweep width (FIG. 3A). Clearly, this initial 1H NMR spectrum of the entire venom is not suited to identify compounds. Its main value consists in providing a record or fingerprint of the original composition of the natural material. In addition, it might contain hints for the presence of unusual small molecules.

NMR signals derived from small molecules generally tend to be well resolved, standing out from those of proteins and polypeptides. In the case of the nucleoside-derived components, in which we had a particular interest, the anomeric proton of the ribose occurs in an uncongested region of the spectrum between 5.9-6.2 ppm, while fucose methyl groups are fairly distinct at 1.2-1.4 ppm. Close inspection of the spectrum in these regions immediately suggested the presence of 10 or more ribonucleoside derivatives, some of which appeared to be fucosylated. NMR signals of the aromatic head groups of acylpolyamines, those of free polyamine chains, as well as those of citric acid and some amino acids are also easily discernable (FIG. 3A).

For further characterization of this mixture, a phase-sensitive dqf-COSY spectrum was acquired. It was found that this technique has significant advantages over the use of traditional magnitude-mode COSY or TOCSY spectra. Especially the predictable antisymmetric shape of all cross-peaks and the embedded multiplicity patterns helped distinguish individual cross peaks clearly from artifacts and each other, which given the enormous degree of overlap was of prime importance for the analysis. Furthermore, analysis of the cross peak multiplicity patterns allowed for determining fairly accurate values for all coupling constants in the various proton spin systems. A small section of the dqf-COSY of the crude venom is shown in FIG. 3B.

Starting with the anomeric protons of the ribose units around 6 ppm, signals representing the other ribose protons were identified in this dqf-COSY. The 0.5 ppm downfield shift of the signals of the methylene protons in the 5' position of the ribose (which is consistent with that of HF-7) indicated some form of derivatization at this position. Because the dqf-COSY cross peaks of these methylenes did not show any additional splitting as would be expected for a phosphorylated residue, it was hypothesized that the 5' position of the various riboses might be sulfated. This nicely exemplifies the usefulness of the dqf-COSY technique, which in this case allowed us to assess the multiplicity of the protons in position 5' and thus to exclude 5'-phosphorylation, even though the corresponding signals are completely obscured in the one-dimensional spectra (See, FIG. 3B).

It should be noted that while the relatively simple appearance of the 1H NMR spectrum around 6 ppm made the initial detection of nucleoside derivatives particularly easy, the presence of nucleosides could have been detected just as well from the dqf-COSY alone had the 1H spectrum been more crowded in this region.

Figure 4:
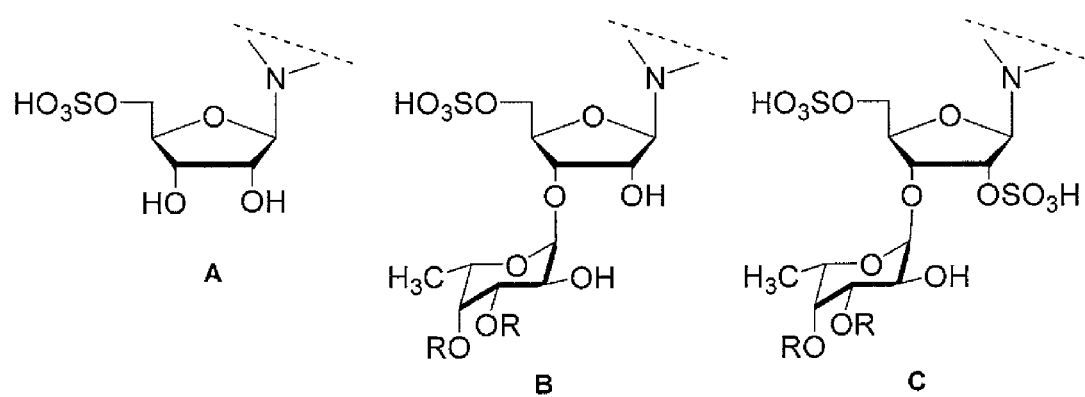
FIG. 4 shows partial structures of sulfated ribonucleosides in *T. agrestis* derived from NMR-spectroscopic analyses of unfractionated venom. Two structures of type A, three structure of type B, and three structures of type C were detected.

In a similar fashion several fucose spin systems were identified from the dqf-COSY, working inward from the anomeric protons and the methyl groups. In order to determine some of the connectivity between the various carbohydrate spin systems thus established, an (1H,13C)-HMBC spectrum of the mixture was acquired, using a variant of the HMBC sequence with improved resolution in F1 (vide infra). Using only NMR spectroscopy of the unfractionated venom for the initial analysis, inventors were able to deduce structures for eight of the ten sulfated nucleosides present in the secretion (See, FIG. 4).

In many cases it was have found that these initial NMR experiments provide more than enough information to determine the structures of the small molecules present, but in the case of *T. agrestis* the situation is quite complex, necessitating the sample be fractionated by HPLC. In this first chromatographic step applied to the native venom, the HPLC peaks tended to be fairly broad, possibly due to the aggregation of the acidic and basic molecules. The venom was roughly divided into early, middle and late eluting fractions with the two earlier eluting fractions containing nucleoside derivatives and the later eluting fraction containing polyamines and peptides. When, after evaporation of the solvent, the contents of the first fraction were examined, the inventors expected to find a mixture of the most polar, bis-sulfated ribonucleosides that they had tentatively identified via analysis of the unfractionated venom (type C in FIG. 4). However, what should have been several different compounds, turned out to be primarily mono-sulfated guanosine and free fucose, while the expected bis-sulfated ribonucleosides were absent.

As pointed our earlier, the spectra of the entire natural secretion do not only provide structural data, but they also serve as a historical record as to the original composition of the mixture. Much like a crime scene photograph used by a forensic scientist, these spectra allow for a comparison of conclusions reached (proposed structures) with the original mixture. If the "identified" natural products are not present in the original spectra, then the molecules may have undergone chemical changes during the purification and analysis, resulting in an "unnatural" natural product. This is exemplified by analysis of the bis-sulfated structures (type C in FIG. 4). While contained within the venom mixture, these molecules are invariably buffered by polyamines, citric acid and inorganic salts. However, it was found that when isolated in their pure forms, these bis-sulfated, glycosylated nucleosides are quite unstable and quickly decompose into mono-sulfated guanosine and fucose. Thus, comparing the isolated molecules with the original data of the crude secretion, it was determined that the natural products were undergoing decomposition. The addition of a small amount of d5-pyridine to each HPLC fraction preserved the molecules as the d5-pyridine salts of their natural form.

To improve separation, an isolation protocol involving reversed-phase HPLC with a 3.4 mM trifluoroacetic acid (TFA)/water and methanol gradient was used. This small amount of TFA is sufficient enough to protonate amino groups and reduce affinity of the sulfates to the column material, without lowering the pH enough to break the glycosidic linkages or to induce partial loss of sulfate. (Similar concentrations of acetic acid and ammonia proved to be significantly less effective at improving the HPLC separation). In order to diminish the risk of decomposition upon concentration, the nucleoside-containing fractions were neutralized immediately after collection by the addition of appropriate amounts of pyridine-d5 (as had been necessary to preserve the bis-sulfated molecules). Fractions of interest were then reexamined by 1H NMR and dqf-COSY, and the resulting spectra compared back to the crude data, which confirmed that there was no noticeable product degradation. In order to obtain 13C data for the isolated compounds investigators had to rely entirely on HMBC and HSQC experiments, because the amounts of material available were very small, which is not surprising given that the entire analysis was based on only 250 µl (100 mg dry weight) of venom.

HMBC experiments were particularly important when analyzing the T. agrestis nucleosides, allowing the inventors to establish the position of the glycosidic linkages. It is rather difficult to achieve this with other techniques such as, for example, mass spectrometry, due to the molecules immediately fragmenting into their basic ring systems, which may not allow one to distinguish between several similar structures (Zaia, J. Mass Spec. Rev., 2004, 23, 161-227; Von Seggern, C. E.; Moyer, S. C.; Cotter, R. J. Anal. Chem. 2003, 75, 3212-3218; Harvey, D. H. Mass Spectrom. Rev. 1999, 18, 349-451, the entire teachings of which are herein incorporated by reference). The need for HMBC spectra presented a major bottle neck in the analysis, since it is the least sensitive among the 2D NMR spectra required for structural assignment, and thus the number of compounds that were able to be characterized was primarily limited by the sensitivity of the specific version of the general HMBC experiment. The use of a non-gradient version of the HMBC sequence without evolution of (1H,1H) couplings during t1 helped increase sensitivity and clear up spectra of mixtures in cases of overlap.

Figure 5:
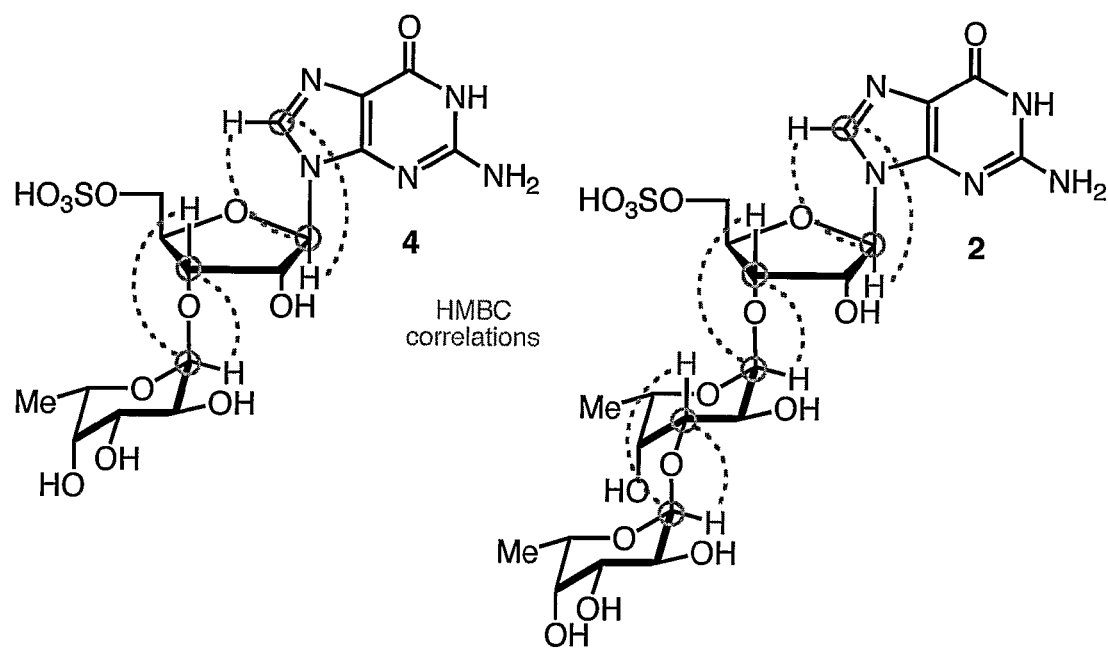
FIG. 5 shows select HMBC correlations used to determine the position of the glycosidic linkages in 2 and 4.

Using this specific HMBC version investigators were able to observe C—H correlations from the ribose to the fucose, and vice versa, thus establishing the connectivity of the sugars in compounds 2 and 4 (FIG. 5). It is notable that these compounds were found to be quite insoluble in aprotic NMR solvents, which derailed an attempt to infer the position of the glycosidic linkages by the absence or presence of hydroxyl protons on the ribose or fucose moieties.

Figure 6:
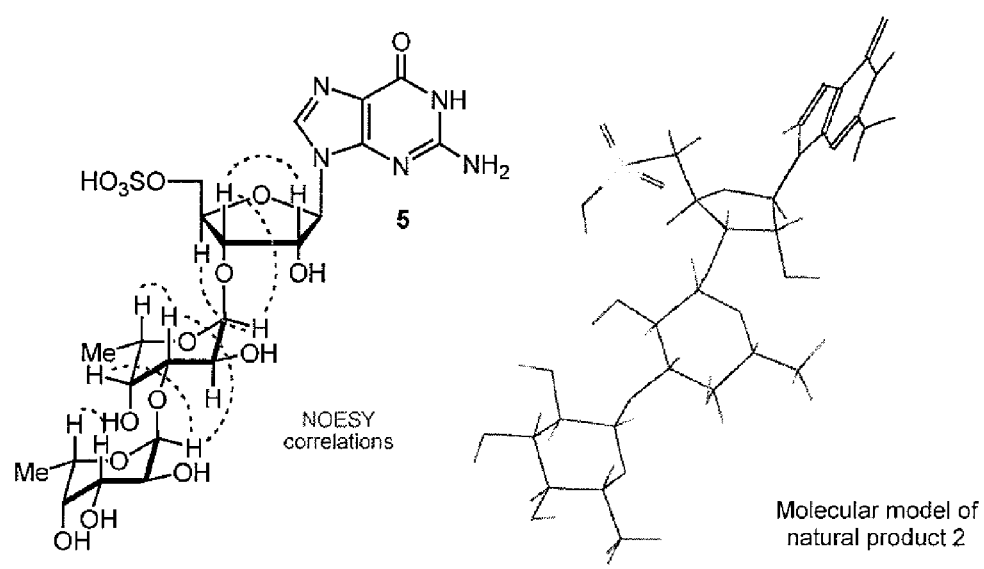
FIG. 6 shows select NOESY correlations and a molecular model of natural product 2 that were used to assign the stereochemistry and connectivity of the sugars.

NOESY experiments were helpful in assigning the configuration of the hexoses in compounds 2 and 4. NOE's observed for the axial protons corroborated the assignment of these 6-deoxyhexoses as fucoses, which originally had been based on coupling constant data obtained from dqf-COSY spectra. Of importance were also the NOE's between the protons in the 1 and 4 positions on the fucoses and the 2 and 3 protons of the ribose in compound 2 (FIG. 6). These ribose-fucose and fucose-fucose correlations corroborated the proposed glycosidic linkages. A molecular mechanics model (Macromodel, Amber force field) of 2 confirms the validity of the observed NOE's, by demonstrating the proximity of the 1" and the 3' and 4' protons as well as the 1'" and the 3" and 4" protons.

Figure 7:
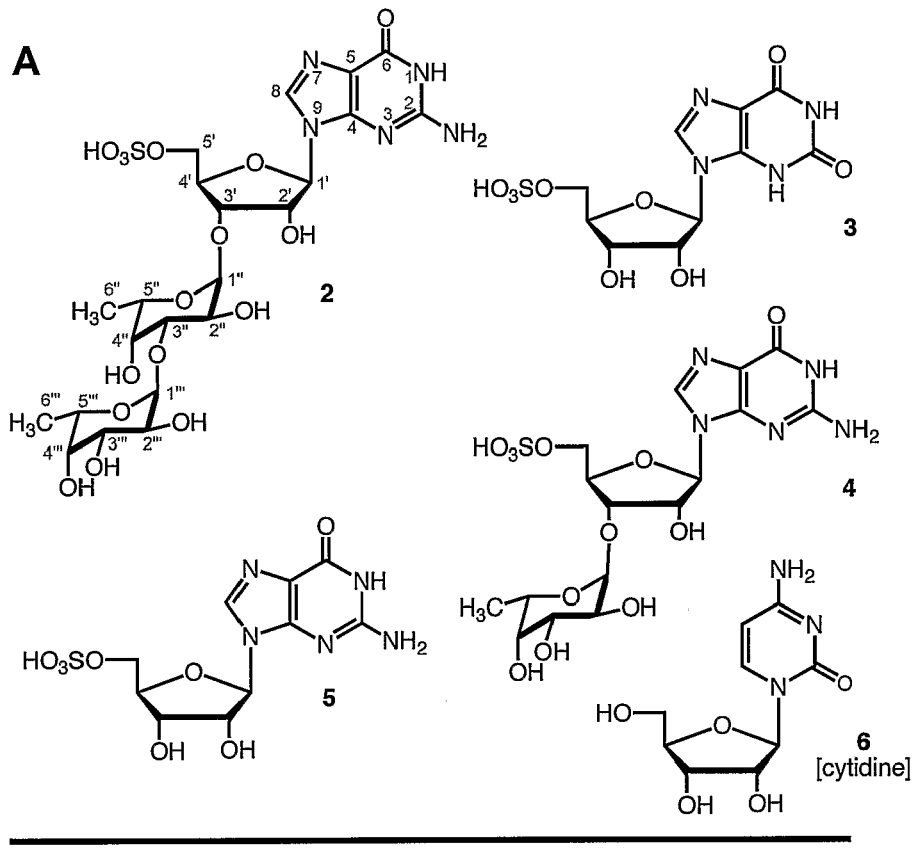
FIG. 7A shows sulfated ribonucleosides 2-5 isolated and identified from *T. agrestis* venom in addition to non-sulfated cytidine (6).
FIG. 7B shows structures 7-9 characterized on the basis of (1H,1H)-dqf-COSY, UV, and electrospray MS only.
Figure 7:
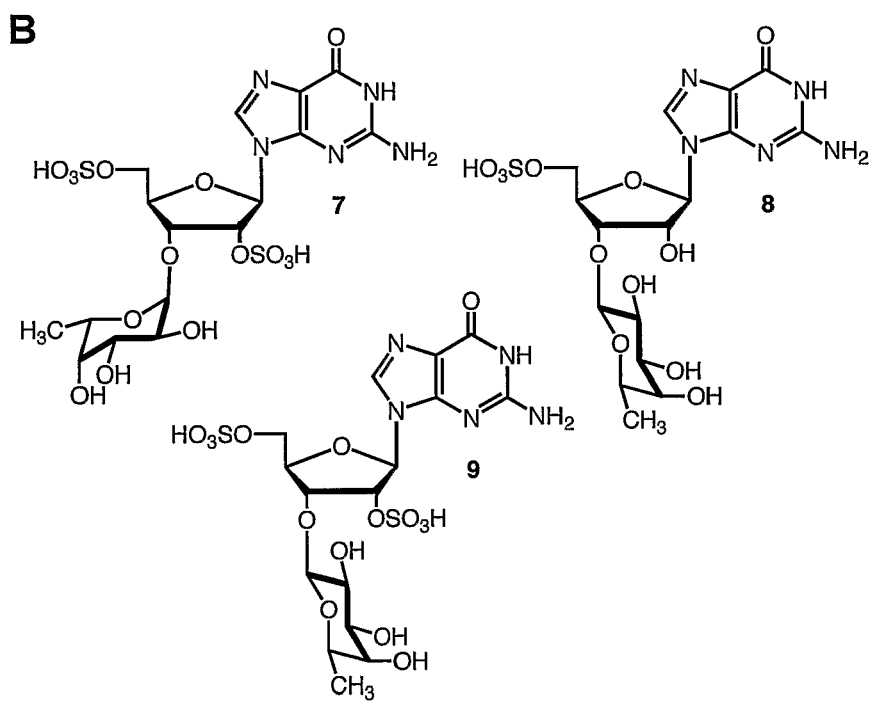

As the last step in the analysis, mass spectra of the isolated compounds via negative-ion electrospray ionization was acquired, which compared to other ionization techniques, gave the best results for this group of compounds. The MS data this obtained allowed investigators to corroborate the presence of sulfate substituents and finalize the assignment of the various nucleic bases (See, FIG. 7A).

The nucleoside containing fraction of *T. agrestis* venom represents about 50% (17 mg) of its total dry weight; the balance being made up of acylpolyamines, peptides, proteins, citrate, and inorganic salts. With the limited amount of *T. agrestis* venom available, investigators were able to completely characterize four sulfated ribonucleosides (2-5) and tentatively identify another three compounds (7-9), in addition to traces of HF-7 (1). For compounds 7-9, investigators were unable to get sufficiently good HMBC spectra, because these compounds occur only at low concentrations in the venom (See, FIG. 7B).

The most abundant molecule in the entire venom is 5'-sulfated guanosine (5), which is found in approximately twice the molar concentration of that of all other nucleosides combined. From the crude NMR data, the molecule is actually present in the natural extract, and is not the result of the degradation of the glycosylated or bis-sulfated compounds. Most of the other ribonucleosides identified in the venom appear to be glycosylated derivatives of 5. Compound 4 has an Q-fucose in the 3' position similar to HF-7 (1). Much like 4, component 2 has a 3' α-fucose to which is attached a second α-fucose. Interestingly, the second fucose moiety in 2 is attached in the 3" position rather than the 4" position, which is where the acyl group in HF-7 (1) is located. Compound 7 is a 2',5'-bis-sulfated guanosine, again with an α-fucose at 3'.

Furthermore, the venom contains traces of the several 3'-β-fucosylated derivatives of 5, most prominently the monosulfated 8. The β-fucose linkage in 8 was inferred from the coupling constant of the anomeric fucose proton (J1"-2"=8.3 Hz), which is more than twice that of the same proton in 4 (J1"-2"=4.0 Hz). Generally, the concentration of the guanosine derivatives in the venom decreases as more functionality is added to the basic 5'-sulfated core. In addition to the guanosines, 5'-sulfated xanthosine (3) and cytidine (6) are present in the mixture, along with very small amounts of corresponding fucosylated derivatives.

The development of improved methods for the discovery of biologically active natural products has been the subject of intense discussion. There are at least two important issues that need be addressed: a) frequent disregard of the biological characteristics of the source organism; and b) a lack of control over the impact that extraction and fractionation procedures have on the biological material. To some extent, the first problem is being addressed by efforts in Chemical Ecology designed to better characterize the organisms of interest biologically, in an effort to derive clues for interesting chemistry from the observation of specific ecological or biochemical phenomena.

From a chemist's point of view, the second issue is particularly worrisome. It is the natural products chemist's bane that they usually know very little about the chemical properties of the compounds they are after. Choice of solvent, chromatography, and other fractionation conditions usually cannot be fine-tuned to the specific chemical properties of the natural product of interest simply because its structure is not yet determined. As a result, a standard regimen of extraction and purification schemes has evolved, which is often applied without much regard to the source of the extract. To what extent these natural product extraction and fractionation schemes can skew the analytical results has, in our opinion, not generally been appreciated.

The present analysis of the venom of Tegenaria agrestis drastically exposes the pitfalls of such a generalized approach to natural products discovery. A significant and from a bioprospecting point of view certainly promising family of compounds making up more than 50% of the biological material under investigation is easily lost using standard chromatographic techniques. Reexamination of the venom of Hololena curta, the original source of the kainate inhibitor HF-7, using our "Direct NMR" method immediately revealed the presence of at least five additional sulfated ribonucleosides, including several of the Tegenaria compounds 2-5 and 7-9. (These structures are currently being established by NMR spectroscopy.) In fact, in the brief amount of time in which the spider venom was analyzed in this way, investigators have found sulfated nucleosides in venoms of at least 12 of the 70 spider species investigated. Clearly, NMR-spectroscopic analyses of unfractionated materials represent an extremely valuable tool for finding new and interesting classes of secondary metabolites.

The difficulties encountered while characterizing these compounds suggests that in the past the discovery of sulfated nucleosides (and glycosides) may have been hampered by their specific chemical properties as well as by the simple fact that during mass spectroscopic analysis they could conceivably be mistaken for the more ubiquitous phosphates since their molecular weight only differs by one AMU. Furthermore, sulfated nucleosides do not ionize very well under electrospray conditions and produce a relatively weak molecular ion, which makes their detection by mass spectroscopy even less likely. It seems possible that sulfated nucleosides have been overlooked in many places. The occurrence of sulfated nucleosides in nature might, therefore, not be limited to spider venom.

Surprisingly, a literature search revealed very little synthetic information about these relatively simple molecules and the biological properties of sulfated ribonucleosides such as 2-5 and 7-9 have not been evaluated. They are remotely related to the herbicidal 5'-sulfamoyl-nucleosides isolated from the bacteria *Streptomyces albus* (R 2374), as well as to a family of phosphorylated nucleosides called adenophostins that affect calcium release (Jenkins, D. J.; Potter, B. V. L. Carbohydr. Res. 1996, 287, 169-182; Hotoda, H.; Takahashi, M.; Tanzawa, K.; Takahashi, S.; Kaneko, M. Tetrahedron Lett. 1995, 36, 5037-5040, the entire teachings of which are herein incorporated by reference). For all of their structural simplicity, the sulfated nucleosides 2-5 and 7-9 may prove to be ingenious inhibitors of biological pathways involving phosphorylated nucleic acids, in addition to their likely potential as neurotoxins. While the sulfate functionality should be sterically somewhat similar to a mono-phosphate, its chemistry can be expected to be quite different. It would be particularly interesting to evaluate sulfated ribonucleosides, or corresponding deoxyribonucleoside derivatives, with regard to potential activity as antivirals or as inhibitors of cell cycle progression. Clearly, the amounts of 2-5 and 7-9 that can be isolated from Tegenaria agrestis will not be sufficient to investigate any of these properties. Syntheses and studies of biological activity will be reported in due course.

In another embodiment, the invention is directed to a method of producing an anti-serum directed to neurotoxins contained within venom. In one aspect, the origin of the venom is from arachnids. In a particular aspect, the venom originates from the Hobo Spider, Tegenaria agrestis.

In one aspect, the inventors contemplate the use of antibodies, either monoclonal or polyclonal which bind to one or more of the compounds disclosed herein. Means for preparing and characterizing antibodies are well known in the art (see, e.g., Harlow and Lane, 1988; the entire teaching of which is incorporated herein by reference). The methods for generating monoclonal antibodies (mAbs) generally begin along the same lines as those for preparing polyclonal antibodies. Briefly, a polyclonal antibody is prepared by immunizing an animal with an immunogenic composition in accordance with the present invention and collecting antisera from that immunized animal. A wide range of animal species can be used for the production of antisera. Typically the animal used for production of anti-antisera is a rabbit, a mouse, a rat, a hamster, a guinea pig or a goat. Because of the relatively large blood volume of rabbits, a rabbit is a preferred choice for production of polyclonal antibodies.

As is well known in the art, a given composition may vary in its immunogenicity. It is often necessary therefore to boost the host immune system, as may be achieved by coupling a peptide or polypeptide immunogen to a carrier. Exemplary carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimide and bis-biazotized benzidine.

As is also well known in the art, the immunogenicity of a particular immunogen composition can be enhanced by the use of non-specific stimulators of the immune response, known as adjuvants. Exemplary adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster, injection may also be given. The process of boosting and titering is repeated until a suitable titer is achieved. When a desired level of immunogenicity is obtained, the immunized animal can be bled and the serum isolated and stored, and/or the animal can be used to generate mAbs.

Monoclonal-Abs can be readily prepared through use of well-known techniques, such as those exemplified in U.S. Pat. No. 4,196,265 (the entire teaching of which is incorporated herein by reference). Typically, this technique involves immunizing a suitable animal with a selected immunogen composition, e.g., a purified or partially purified crystal protein, polypeptide or peptide. The immunizing composition is administered in a manner effective to stimulate antibody producing cells. Rodents such as mice and rats are typical animals, however, the use of rabbit, sheep frog cells is also possible. The use of rats can provide certain advantages (Goding, 1986, pp. 60-61), but mice are quite typical, with the BALB/c mouse being often employed as this is most routinely used and generally gives a higher percentage of stable fusions.

Following immunization, somatic cells with the potential for producing antibodies, specifically B lymphocytes (B cells), are selected for use in the mAb generating protocol. These cells can be obtained from biopsied spleens, tonsils or lymph nodes, or from a peripheral blood sample. Spleen cells and peripheral blood cells are typical sources, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures are non-antibody-producing, have high fusion efficiency, and enzyme deficiencies that render then incapable of growing in certain selective media which support the growth of only the desired fused cells (hybridomas).

Any one of a number of myeloma cells can be used, as are known to those of skill in the art (Goding, pp. 65-66, 1986; Campbell, pp. 75-83, 1984; the entire teachings of which are incorporated herein by reference). For example, where the immunized animal is a mouse, one can use P3-X63/Ag8, X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions.

One typical murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 ratio, though the ratio can vary from about 20:1 to about 1:1, respectively, in the presence of an agent or agents (chemical or electrical) that promote the fusion of cell membranes. Fusion methods using Sendai virus have been described (Kohler and Milstein, 1975; 1976, the entire teaching of which is incorporated herein by reference), and those using polyethylene glycol (PEG), such as 37% (vol./vol.) PEG, (Gefter et al., 1977, the entire teaching of which is incorporated herein by reference). The use of electrically induced fusion methods is also appropriate (Goding, 1986, pp. 71-74, the entire teaching of which is incorporated herein by reference).

Fusion procedures usually produce viable hybrids at low frequencies, about $1 \times 10^{-6}$ to $1 \times 10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media, exemplary agents include, but are not limited to, aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

A typical selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B-cells can operate this pathway, but they have a limited life span in culture and generally die within about two weeks. Therefore, the only cells that can survive in the selective media are those hybrids formed from myeloma and B-cells. This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide mAbs. The cell lines can be exploited for mAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide mAbs in high concentration. The individual cell lines could also be cultured in vitro, where the mAbs are naturally secreted into the culture medium from which they can be readily obtained in high concentrations. Monoclonal-Abs produced by either means may be further purified, if desired, using filtration, centrifugation and various chromatographic methods such as HPLC or affinity chromatography.

Compounds of the present invention, including their respective derivatives, can be used to elicit an immunological response. This process can be used to sensitize a subject's immune system to one or more of the present invention's compounds. In another aspect, an animal can be subjected to one or more of the compounds of the present invention wherein an immunological response is produced. In this scenario, the serum from the animal can be collected and prepared to be used later in the course of treating a person subjected to the introduction of venom.

Based fundamentally upon the principles of immunization, the present invention is directed to immunizing an individual against one or more of the compounds of the present invention. Immunization is a process of administering an antigen, either alone or in combination with another molecule that will assist in eliciting an immune response, to an individual for the purpose of inducing an immune response to the antigen.

Immunization (or vaccination) was developed primarily as a prophylactic measure to prevent disease caused by infectious agents, and, provided that their use caused only low levels of morbidity and especially mortality. Venoms can also be subject to prophylactic regimes. That is, as vaccines are used to maintain a certain surveillance level of antibodies to fight off bacteria and viral-based diseases, antibodies directed toward components of venom that are responsible for triggering a disease state in an individual can be useful in arresting these venom components. The efficacy of such vaccinations using compounds of the present invention can be assessed by, for example, examining antibody titers. This is known and can be performed by one skilled in the art.

In another aspect, serum preparations can be manufactured for human and animal use through methods well known to those skilled in the art. These serum products, comprising necessary elements including, but not limited to, antibodies directed against one or more of the venom-based compounds of the present invention, can be used for treatment regimes for those subjects in which venom has been introduced. In one particular aspect, the venom is from a spider. In this embodiment, the afflicted subject is administered an effective amount of serum so as to alleviate or stop any pathology and associated symptomology due to the venom. A person skilled in the art can determine what the appropriate effective amount is without undue experimentation.

Those skilled in the art can determine dosage regimes without undue experimentation. For example, by employing the technique of monitoring antibody titer, a practitioner can determine the dosage and time interval for administration.

In another embodiment, one or more compounds (including derivatives thereof) of the present invention are used to treat diseases associated with nuclear events in a cell. These invents include, but are not limited to, nucleic acid replication, transcription, and/or translation. In one aspect, the compounds of the present invention can be used to interrupt agents affecting the cell biology of a subject.

Certain disease processes are facilitated by agents that operate at the cellular level. Some disease states involve mechanism affecting the genome of an affected subject. Cancer represents an example of diseases that affect the cell biology of an individual. In simple terms, cancers can be viewed as cells out of control with respect to their growth. The ability to regulate growth, viz. cellular division, is attenuated. The growth of a tumor involves, among other factors, cell division. Cell division in turns requires the replication of the genetic material, namely, DNA. Disruption of an affected cell's ability to divide hampers tumor growth and, hence, arrests the disease.

There are other diseases that involve the transcription and/or translational apparatus of an affected cell. For example, some viruses infect a host cell and commandeer the host cell's transcriptional and/or translational machinery. Viral growth is dependent upon a virus' ability to replicate its genome and produce the necessary viral proteins associated with that particular virus. If a therapeutic agent could interrupt a virus' ability to synthesize copies of its genome and the necessary viral proteins, then the viral infection can be attenuated.

The venom-based compounds of the present invention can be used to treat subjects afflicted with a disease whose pathology includes the disruption of cellular events such as replication of nucleic acids, transcription, and/or translation. An effective amount of one or more compounds of the present invention can be administered to an affected subject. An effective amount is to be understood as that amount which arrests or minimizes the pathological process, relieves symptoms experienced by the affected subject or a combination of both.

Any of the identified compounds of the present invention can be administered to a subject, including a human, by itself, or in pharmaceutical compositions where it is mixed with suitable carriers or excipients at doses therapeutically effective to prevent, treat or ameliorate a variety of disorders, including those characterized by that outlined herein. A therapeutically effective dose further refers to that amount of the compound sufficient result in the prevention or amelioration of symptoms associated with such disorders. Techniques for formulation and administration of the compounds of the instant invention may be found in Goodman and Gilman's The Pharmacological Basis of Therapeutics, Pergamon Press, latest edition.

The compounds of the present invention can be targeted to specific sites by direct injection into those sites. Compounds designed for use in the central nervous system should be able to cross the blood-brain barrier or be suitable for administration by localized injection.

Pharmaceutical compositions suitable for use in the present invention include compositions wherein the active ingredients are contained in an effective amount to achieve its intended purpose. More specifically, a therapeutically effective amount means an amount effective to prevent development of or alleviate the existing symptoms and underlying pathology of the subject being treating. Determination of the effective amounts is well within the capability of those skilled in the art.

For any compound used in the methods of the present invention, the therapeutically effective dose can be estimated initially from cell culture assays. For example, a dose can be formulated in animal models to achieve a circulating concentration range that includes the IC50 (the dose where 50% of the cells show the desired effects) as determined in cell culture. Such information can be used to more accurately determine useful doses in humans.

A therapeutically effective dose refers to that amount of the compound that results in the attenuation of symptoms or a prolongation of survival in a subject. Toxicity and therapeutic efficacy of such compounds can be determined by standard pharmaceutical procedures in cell cultures or experimental animals, e.g., for determining the LD50 (the dose lethal to 50% of a given population) and the ED50 (the dose therapeutically effective in 50% of a given population). The dose ratio between toxic and therapeutic effects is the therapeutic index and it can be expressed as the ratio between LD50 and ED50.

Compounds which exhibit high therapeutic indices are preferred. The data obtained from these cell culture assays and animal studies can be used in formulating a range of dosage for use in human. The dosage of such compounds lies preferably within a range of circulating concentrations that include the ED50 with little or no toxicity. The dosage can vary within this range depending upon the dosage form employed and the route of administration utilized. The exact formulation, route of administration and dosage can be chosen by the individual physician in view of a patient's condition. Dosage amount and interval can be adjusted individually to provide plasma levels of the active moiety that are sufficient to maintain the desired effects.

In case of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

The pharmaceutical compositions of the present invention can be manufactured in a manner that is itself known, e.g., by means of conventional mixing, dissolving, granulating, levigating, emulsifying, encapsulating, entrapping or lyophilizing processes.

Pharmaceutical compositions for use in accordance with the present invention thus can be formulated in conventional manner using one or more physiologically acceptable carriers comprising excipients and auxiliaries that facilitate processing of the active compounds into preparations which can be used pharmaceutically. Proper formulation is dependent upon the route of administration chosen.

For injection, the agents of the invention can be formulated in aqueous solutions, preferably in physiologically compatible buffers such as Hank's solution, Ringer's solution, or physiological saline buffer. For transmucosal administration, penetrants appropriate to the barriers to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carboxymethylcellulose, and/or polyvinyl-pyrrolidone (PVP). If desired, disintegrating agents can be added, such as the cross-linked polyvinyl pyrrolidone, agar, or alginic acid or a salt thereof such as sodium alginate.

Dragee cores are provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration.

For buccal administration, the compositions can take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoromethane, carbon dioxide or other suitable gas. In the case of a pressurized aerosol the dosage unit can be determined by providing a valve to deliver a metered amount. Capsules and cartridges of e.g., gelatin for use in an inhaler or insufflator can be formulated containing a powder mix of the compound and a suitable powder base such as lactose or starch.

The compounds can be formulated for parenteral administration by injection, e.g., by bolus injection or continuous infusion. Formulations for injection can be presented in unit dosage for, e.g., in ampoules or in multidose containers, with added preservatives. The compositions can take such forms as suspensions, solutions or emulsions in oily or aqueous vehicles, and can contain formulatory agents such as suspending, stabilizing and/or dispersing agents.

Pharmaceutical formulations for parenteral administration include aqueous solutions of the active compounds in water-soluble form. Additionally, suspensions of the active compounds can be prepared as appropriate oily injection suspension. Suitable lipophilic solvents or vehicles include fatty oils such as sesame oil, or synthetic fatty acid esters, such as ethyl oleate or triglycerides, or liposomes. Aqueous injection suspensions can contain substances that increase the viscosity of the suspension, such as sodium carboxymethyl cellulose, sorbitol, or dextran. Optionally, the suspension can also contain suitable stabilizers or agents that increase the solubility of the compounds to allow for the preparation of highly concentrated solutions.

Alternatively, the active ingredient can be in powder form for constitution with a suitable vehicle, e.g., sterile pyrogen-free water, before use.

The compounds can also be formulated in rectal compositions such as suppositories or retention enemas, e.g., containing conventional suppository bases such as cocoa butter or other glycerides.

In addition to the formulations previously described, the compounds can also be formulated as a depot preparation. Such long acting formulations can be administered by implantation (e.g., subcutaneously or intramuscularly) or by intramuscular injection. Thus, for example, the compounds can be formulated with suitable polymeric or hydrophobic materials (e.g., as an emulsion in an acceptable oil) or ion exchange resins, or as sparingly soluble derivatives, e.g., as a sparingly soluble salt.

A pharmaceutical carrier for the hydrophobic compounds of the invention is a co-solvent system comprising benzyl alcohol, a non-polar surfactant, a water-miscible organic polymer, and an aqueous phase. Naturally, the proportions of a co-solvent system can be varied considerably without destroying its solubility and toxicity characteristics. Furthermore, the identity of the co-solvent components can be varied.

Alternatively, other delivery systems for hydrophobic pharmaceutical compounds can be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds can be delivered using a sustained-release system, such as semipermeable matrices of solid hydrophobic polymers containing the therapeutic agent. Variations of sustained-release materials have been established and are well known to those skilled in the art. Sustained-release capsules can, depending on their chemical nature, release the compounds for a few weeks up to over 100 days. Depending on the chemical nature and the biological stability of the therapeutic reagent, additional strategies for protein stabilization can be employed.

The pharmaceutical compositions also can comprise suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols.

Many of the compounds of the invention can be provided as salts with pharmaceutically compatible counter ions. Pharmaceutically compatible salts can be formed with many acids, including but not limited to hydrochloric, sulfuric, acetic, lactic, tartaric, malic, succinic, etc. Salts tend to be more soluble in aqueous or other protonic solvents that are the corresponding free base forms.

Suitable routes of administration can, e.g., include oral, rectal, transmucosal, transdermal, or intestinal administration; parenteral delivery, including intramuscular, subcutaneous, intramedullary injections, as well as intrathecal, direct intraventricular, intravenous, intraperitoneal, intranasal, or intraocular injections.

Alternatively, one can administer the compound in a local rather than systemic manner, e.g., via injection of the compound directly into an affected area, often in a depot or sustained release formulation.

Furthermore, one can administer the compound in a targeted drug delivery system, e.g., in a liposome coated with an antibody specific for affected cells. The liposomes will be targeted to and taken up selectively by the cells.

The compositions can, if desired, be presented in a pack or dispenser device that can contain one or more unit dosage forms containing the active ingredient. The pack can, e.g., comprise metal or plastic foil, such as a blister pack. The pack or dispenser device can be accompanied by instruction for administration. Compositions comprising a compound of the invention formulated in a compatible pharmaceutical carrier can also be prepared, placed in an appropriate container, and labeled for treatment of an indicated condition. Suitable conditions indicated on the label can include treatment of a disease such as described herein.

EXAMPLE

Below is a protocol for the preparation of sulfated nucleosides: three-step synthesis of ((2R,3R,4S,5R)-5-(2-amino-6-oxo-1,6-dihydropurin-9-yl)-3,4-dihydroxy-tetrahydrofuran-2-yl)methyl hydrogen sulfate (5, below).

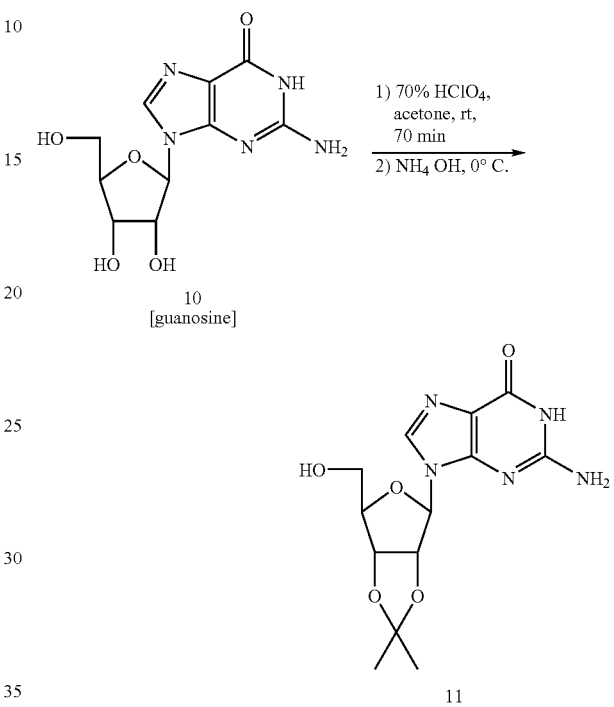

2-amino-9-(6-(hydroxymethyl)-2,2-dimethyl-tetrahydrofuro[3,4-d][1,3]dioxol-4-yl)-1H-purin-6(9H)-one (11). To a slurry of guanosine (0.25 g, 1.0 eq) (10) and acetone (15 mL) at room temperature was added 70% HClO4 (0.103 mL, 1.35 eq). The reaction was stirred for approximately 70 minutes, at which time it was clear and colorless. The reaction was then cooled to 0° C. in an ice/water bath and concentrated NH4OH (0.167 mL, 1.41 eq) was added causing the formation of a milky white, gelatinous precipitate. The precipitate was collected on filter paper, resulting in a white papery solid that was dried at reduced pressure and ambient temperature for approximately 1 hour yielding 11 (0.262 g, 92%).

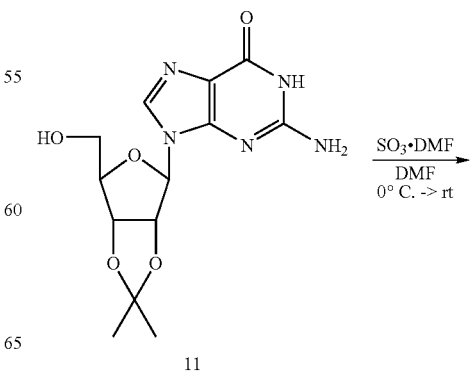

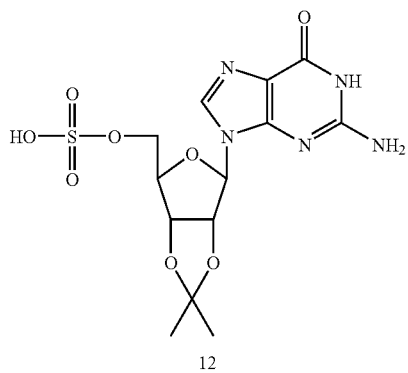

12

(6-(2-amino-6-oxo-1,6-dihydropurin-9-yl)-2,2-dimethyl-tetrahydrofuro[3,4-d][1,3]dioxol-4-yl)methyl hydrogen sulfate (12). To a solution of SO3.DMF (0.248 g, 2.0 eq) in DMF (1.5 mL) at 0° C. was added a solution of 11 (0.262 g, 1 eq) in DMF (1.5 mL). The reaction was allowed to gradually warm to room temperature overnight. Enough KHCO3 to coat the bottom of the flask was added, and the reaction was allowed to stir for another 15 minutes. The reaction was then filtered through celite and concentrated yielding 12, which was used without purification.

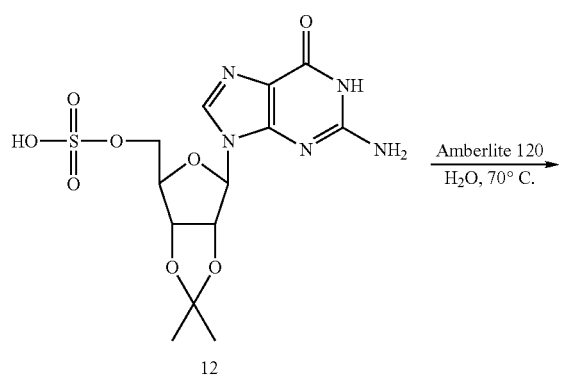

12

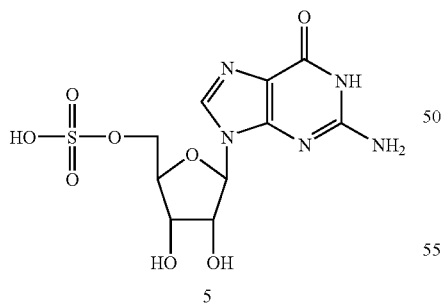

5

((2R,3R,4S,5R)-5-(2-amino-6-oxo-1,6-dihydropurin-9-yl)-3,4-dihydroxytetrahydro-furan-2-yl)methyl hydrogen sulfate (5). To a solution of crude 12 (8.11 mmol) in water (8 mL) was added Amberlite 120 acidic resin (0.300 g). The mixture was heated to 70° C. for 4 hours, and then filtered while hot through a sintered glass frit. The water was removed under reduced pressure and ambient temperature to yield 5 (0.244 g, 83% for two steps).

With small modifications depending on the exact nature of the carbohydrate unit (for example ribose or 2-deoxyribose) and the nature of the nitrogen-containing heterocyclus (for example guanine, xanthine, thymine, cytosine or uracil), this procedure can be used to prepare a large number of the sulfated nucleosides covered by this invention.

Glycosylated derivatives (for example fucosylated or glycosylated derivatives) can be obtained for example as published in McCormick, J., et al., J. Am. Chem. Soc. 1999, 121, 5661-5665, the teaching of which is incorporated herein in its entirety by reference.

Although the invention has been described with respect to various embodiments, it should be realized this invention is also capable of a wide variety of further and other embodiments within the spirit and scope of the appended claims.

What is claimed is:

1. A compound having a general structure of the formula:

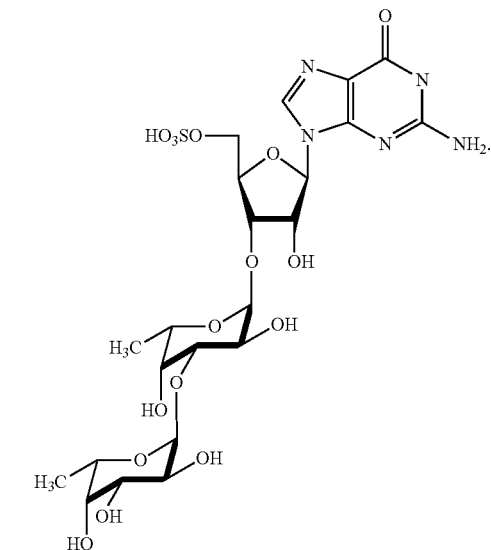

2. A compound having a general structure of the formula:

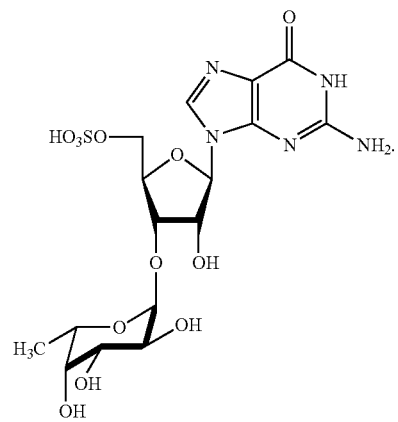

3. A compound having a general structure of the formula:
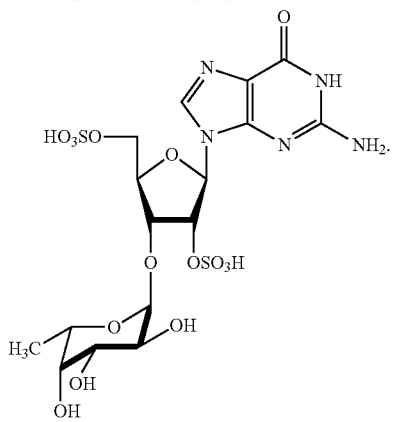
4. A compound having a general structure of the formula:
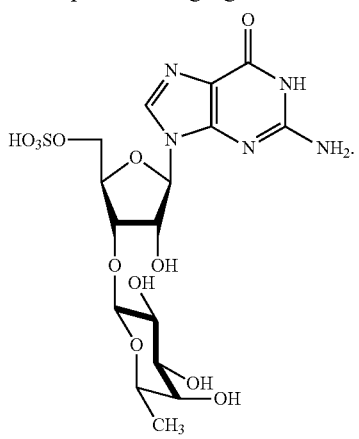
5. A compound having a general structure of the formula:
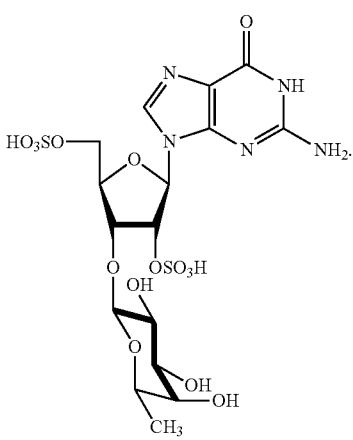
* * * * *